US012622731B2

(12) United States Patent
Bhandari

(10) Patent No.: US 12,622,731 B2
(45) Date of Patent: May 12, 2026

(54) HINGED DORSAL SPANNING PLATE

(71) Applicant: VANDERBILT UNIVERSITY,
Nashville, TN (US)

(72) Inventor: Panambur Laxminarayan Bhandari,
Nashville, TN (US)

(73) Assignee: VANDERBILT UNIVERSITY,
Nashville, TN (US)

( * ) Notice: Subject to any disclaimer, the term of this
patent is extended or adjusted under 35
U.S.C. 154(b) by 0 days.

(21) Appl. No.: 18/928,460

(22) Filed: Oct. 28, 2024

(65) Prior Publication Data

US 2025/0134564 A1 May 1, 2025

Related U.S. Application Data

(60) Provisional application No. 63/595,019, filed on Nov.
1, 2023.

(51) Int. Cl.
A61B 17/80 (2006.01)

(52) U.S. Cl.
CPC ...... A61B 17/8004 (2013.01); A61B 17/8061
(2013.01)

(58) Field of Classification Search
CPC .. A61B 17/80; A61B 17/8004; A61B 17/8061
See application file for complete search history.

(56) References Cited

U.S. PATENT DOCUMENTS

| | | | |
|---|---|---|---|
| 6,183,476 B1 * | 2/2001 | Gerhardt ................ | A61B 17/80 606/71 |
| 2006/0089648 A1 * | 4/2006 | Masini ............... | A61B 17/1615 606/291 |
| 2012/0172997 A1 * | 7/2012 | Thorwarth ............ | A61L 27/306 427/2.26 |
| 2016/0000482 A1 * | 1/2016 | Ehmke ............... | A61B 17/8863 606/71 |

* cited by examiner

*Primary Examiner* — Si Ming Ku
(74) *Attorney, Agent, or Firm* — Thomas | Horstemeyer,
LLP

(57) ABSTRACT

In one aspect, the disclosure relates to a dorsal spanning
plate assembly comprising a first plate member that can be
fixed to a bone or bone fragment distal to a distal radius
fracture and a second plate member that can be fixed to a
bone or bone fragment proximal to the distal radius fracture.
In an aspect, the dorsal spanning plate assembly includes a
joint such as, for example, a hinge joint or a ball-and-socket
joint, wherein the joint is not fixed during placement of the
dorsal spanning plate assembly. In still another aspect, a
subject in whom the dorsal spanning plate assembly is
implanted retains some range of motion in the fractured
joint, thereby reducing muscle atrophy and retaining joint
flexion during recovery. Also disclosed are methods of
setting bone fractures using the dorsal spanning plate assem-
bly.

19 Claims, 4 Drawing Sheets

HINGED DORSAL SPANNING PLATE

CROSS-REFERENCE TO RELATED APPLICATIONS

This application claims priority to, and the benefit of, U.S. provisional application Ser. No. 63/595,019 filed Nov. 1, 2023, which is hereby incorporated by reference in its entirety.

BACKGROUND

Distal radius fractures are common. A dorsal spanning plate is often used to treat such fractures. Typical dorsal spanning plates work by maintaining distraction at the radio carpal joint, which helps in keeping the fracture in reduction. These plates are often used along with volar plates; and are usually removed after 8-12 weeks. One drawback of using conventional dorsal spanning plates plate is that the wrist joint is completely immobilized for 8-12 weeks. This is not only inconvenient for the patient when the plate is in place, but also may limit future range of motion of the wrist as well as contribute to overall muscle weakness around the fracture site. In particular, muscle atrophy can occur when a joint is held immobile for a period of weeks or months, requiring months of physical therapy.

Although some dorsal spanning plates currently in use are equipped with hinges, these hinges merely aid the surgeon in positioning the fractured joint and are fixed or immobilized during implantation surgery once proper positioning of the joint or proper reduction of the fracture is achieved, these are not intended or designed for continued motion of affected joints during fracture healing and will fail if the joint is left unfixed. In fact, in many cases, continued motion after installation would endanger the fracture reduction. Thus, muscle atrophy and decreased range of motion are still risks for patients equipped with these devices.

Despite advances in distal radius fracture heling research, there is still a scarcity of devices that are capable of keeping the fracture in reduction while also allowing for retention of range of motion and providing for decreases in muscle atrophy typically seen with dorsal spanning plates that are fixed in place. These needs and other needs are satisfied by the present disclosure.

SUMMARY

In accordance with the purpose(s) of the present disclosure, as embodied and broadly described herein, the disclosure, in one aspect, relates to a dorsal spanning plate assembly comprising a first plate member that can be fixed to a bone or bone fragment distal to a distal radius fracture and a second plate member that can be fixed to a bone or bone fragment proximal to the distal radius fracture. In an aspect, the dorsal spanning plate assembly includes a joint such as, for example, a hinge joint or a ball-and-socket joint, wherein the joint is not fixed during placement of the dorsal spanning plate assembly. In still another aspect, a subject in whom the dorsal spanning plate assembly is implanted retains some range of motion in the fractured joint, thereby reducing muscle atrophy and retaining joint flexion during recovery. Also disclosed are methods of setting bone fractures using the dorsal spanning plate assembly.

Other systems, methods, features, and advantages of the present disclosure will be or become apparent to one with skill in the art upon examination of the following drawings and detailed description. It is intended that all such additional systems, methods, features, and advantages be included within this description, be within the scope of the present disclosure, and be protected by the accompanying claims. In addition, all optional and preferred features and modifications of the described embodiments are usable in all aspects of the disclosure taught herein. Furthermore, the individual features of the dependent claims, as well as all optional and preferred features and modifications of the described embodiments are combinable and interchangeable with one another.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

Figure 1:
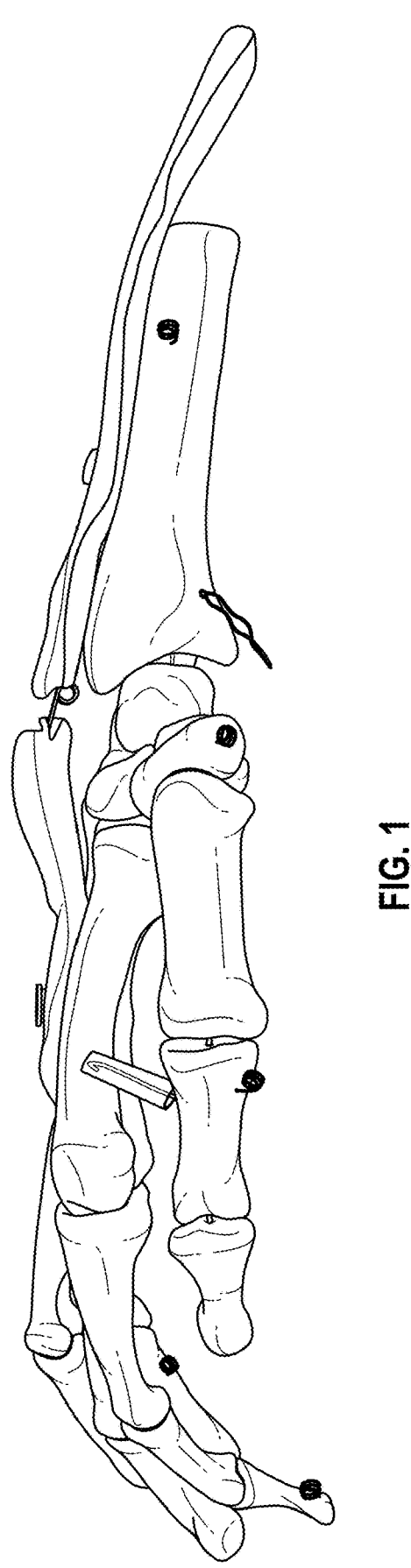
FIG. 1 is a photograph of a side view of a hinged dorsal spanning plate according to the present disclosure, fixed onto a model radio carpal joint, wherein the joint is held in a neutral position.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

Fractured bones are treated using a fixation device that reinforces the bone and keeps bone fragments aligned during healing. Fixation devices may take a variety of forms, including casts for external fixation and bone plates for internal fixation, among others. Bone plates are implantable devices that can be mounted on bone with the plate spanning a fracture. In an aspect, to use a bone plate to repair a fractured bone, a surgeon selects an appropriate plate, reduces (sets) the fracture, and attaches the plate to opposite sides of the fracture using suitable fasteners, such as bone screws, so that pieces of the bone are fixed relative to one another. Bone plates are often formed as one piece and are bent by the surgeon as needed—which may be difficult and weaken the plates—or may include a hinge for positioning of a joint following installation of the plates, but the hinges are fixed in place by the surgeon after positioning, decreasing range of motion and leading to muscle atrophy around the joint.

As a solution to the problem of muscle atrophy and loss of range of motion during healing of distal radius fractures, disclosed herein is a dorsal spanning plate assembly that includes a first plate member that can be fixed to a bone or bone fragment distal to a distal radius fracture and a second plate member that can be fixed to a bone or bone fragment proximal to the distal radius fracture. In an aspect, the dorsal spanning plate assembly includes a joint such as, for example, a hinge joint or a ball-and-socket joint, wherein the joint is not fixed during placement of the dorsal spanning plate assembly. In still another aspect, a subject in whom the dorsal spanning plate assembly is implanted retains some range of motion in the fractured joint, thereby reducing muscle atrophy and retaining joint flexion during recovery. Also disclosed are methods of setting bone fractures using the dorsal spanning plate assembly.

A permanent connection between plate members can be created during manufacture of a the disclosed dorsal spanning plate assembly, such that the plate members always remain connected to one another during normal handling and installation. In one aspect, plate members that are permanently connected to one another are designed never to be accidentally disassembled prior to implantation. In an aspect, a dorsal spanning plate assembly with plate members that are permanently connected to one another at a movable joint offers the advantage of a movable bone plate without the risk of dropping or losing a piece of the joint (e.g., a connector) during surgery.

In some aspects, the disclosed dorsal plate assembly allows for subjects with distal radius fractures to begin active motion of the wrist joint soon after injury, since the dorsal spanning plate assembly offloads pressure from the fracture site. In a further aspect, the dorsal spanning plate assembly allows for an earlier start for any necessary physical therapy and further allows for the patient to conduct non-weight-bearing activities of daily living, ensuring greater independence without the possibility for reinjury of the joint and overall better patient outcomes.

In one aspect, the plate assembly can be removed at 8-12 weeks. Without wishing to be bound by theory, due to the short installation time, there should not be any concerns about longevity of the hinge mechanism.

Hinged Dorsal Spanning Plate

Disclosed herein is a dorsal spanning plate assembly, including at least the following components:

a first plate member, wherein the first plate member has an elongated body defining a first longitudinal axis and including a first proximal end, a first distal end, a first bone contacting surface, and an opposite surface;

a second plate member, wherein the second plate member has an elongated body defining a second longitudinal axis and including a second proximal end, a second distal end, a second bone contacting surface, and an opposite surface and a movable joint connecting the first proximal end to the second distal end, wherein the movable joint is configured to allow subject-directed movement of a radio carpal joint following implantation in a subject.

In an aspect, the first plate member and the second plate member can have any suitable structure. In a further aspect, the plate members may or may not be elongate. In still another aspect, the plate members can have an outer surface opposite an inner surface. Further in this aspect, the inner surface and the outer surface of each plate member respectively face toward and away from a bone when the bone plate is attached to the bone. In one aspect, the inner surface can be a bone contacting surface. In some aspects, each plate member can be one piece, with no parts that move relative to one another without deformation of the plate member.

In a further aspect, the first plate member and the second plate member each include one or more holes. In some aspects, one or more first screws can extend through one of the one or more holes in the first plate member, and one or more second screws can extend through one of the one or more holes in the second plate member. In any of these aspects, the one or more first screws and second screws are suitable for securing a bone or bone fragment. In another aspect, the first bone contacting surface of the first plate member can be in contact with a first bone such as, for example, a metacarpal bone (e.g. metacarpal III), while a second bone contacting surface of the second plate member can be in contact with a second bone such as, for example, the radius. Further in these aspects, the bone screws can be used to secure the hinged dorsal spanning plate assembly to these respective bones to hold the assembly in place. In one aspect, all holes in each of the plate members are used to hold screws. In another aspect, one or more of the holes in each plate member are not used. In still another aspect, a screw is secured in only one hole of each of the plate members. In some aspects, the medical practitioner can decide how many bone screws to use and placement of the same depending on the particular shape and placement of the fracture.

In an aspect, each plate member has at least one opening having a suitable structure and position. In another aspect, each opening can be a through-hole that extends through the plate member from the outer surface to the inner surface thereof. In a further aspect, the through-hole defines an axis that is substantially perpendicular or oblique to the plane of the plate member. In still another aspect, each through-hole or other opening may or may not be elongated in the plane of the plate member, or may or may not be circular. In one aspect, the through-hole or other opening may or may not have attachment structure formed by a wall thereof that allows a fastener, such as an externally threaded fastener, to be attached to the plate member at the through-hole.

In a still further aspect, each plate member can have any suitable number of openings. Further in this aspect, if the plate member has two or more openings, the openings can be distributed in a direction along and/or across the bone plate from one another. In another aspect, each plate member can be marked with surface markings to define a longitudinal region of the plate member that should overlie the fractured or cut portion of the bone to be fixed or for another purpose. In a further aspect, the surface marking can be formed by etching, machining, molding, coating, electrolyzing, or the like at the region to be marked, to make the region or boundaries thereof visibly distinguishable.

In an aspect, the movable joint can be a hinge joint or a ball-and-socket joint. In another aspect, a hinge joint allows flexion and extension of the radio carpal joint in a subject, while a ball-and-socket joint allows three dimensional motion of the radio carpal joint. In any of these aspects, the subject has a distal radius fracture.

In one aspect, the dorsal spanning plate assembly does not include a setting fastener. In another aspect, one or more additional stabilizing wires, pins, or connectors can be used to secure the joint, depending on the shape, placement, and complexity of the fracture.

Figure 2:
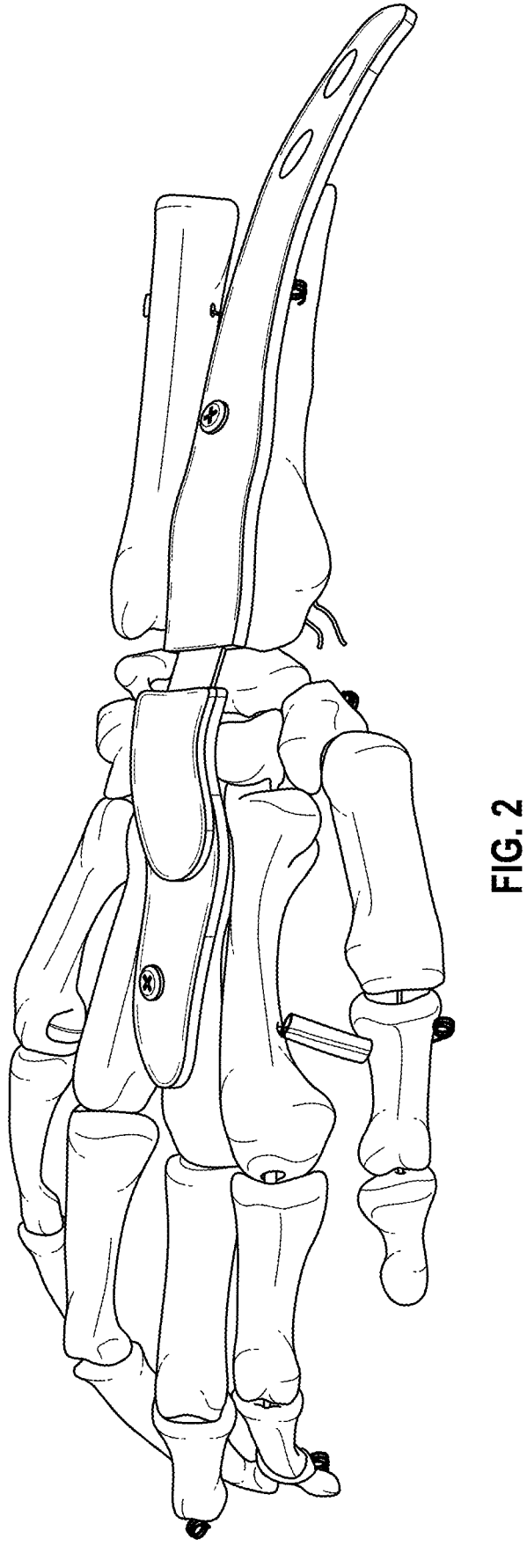
FIG. 2 is a photograph of a top view of a hinged dorsal spanning plate according to the present disclosure, fixed onto a model radio carpal joint. In this view, the joint is in a neutral position and the pistoning mechanism from one piece of the plate is in a shortened or inserted configuration relative to the other piece.
Figure 3:
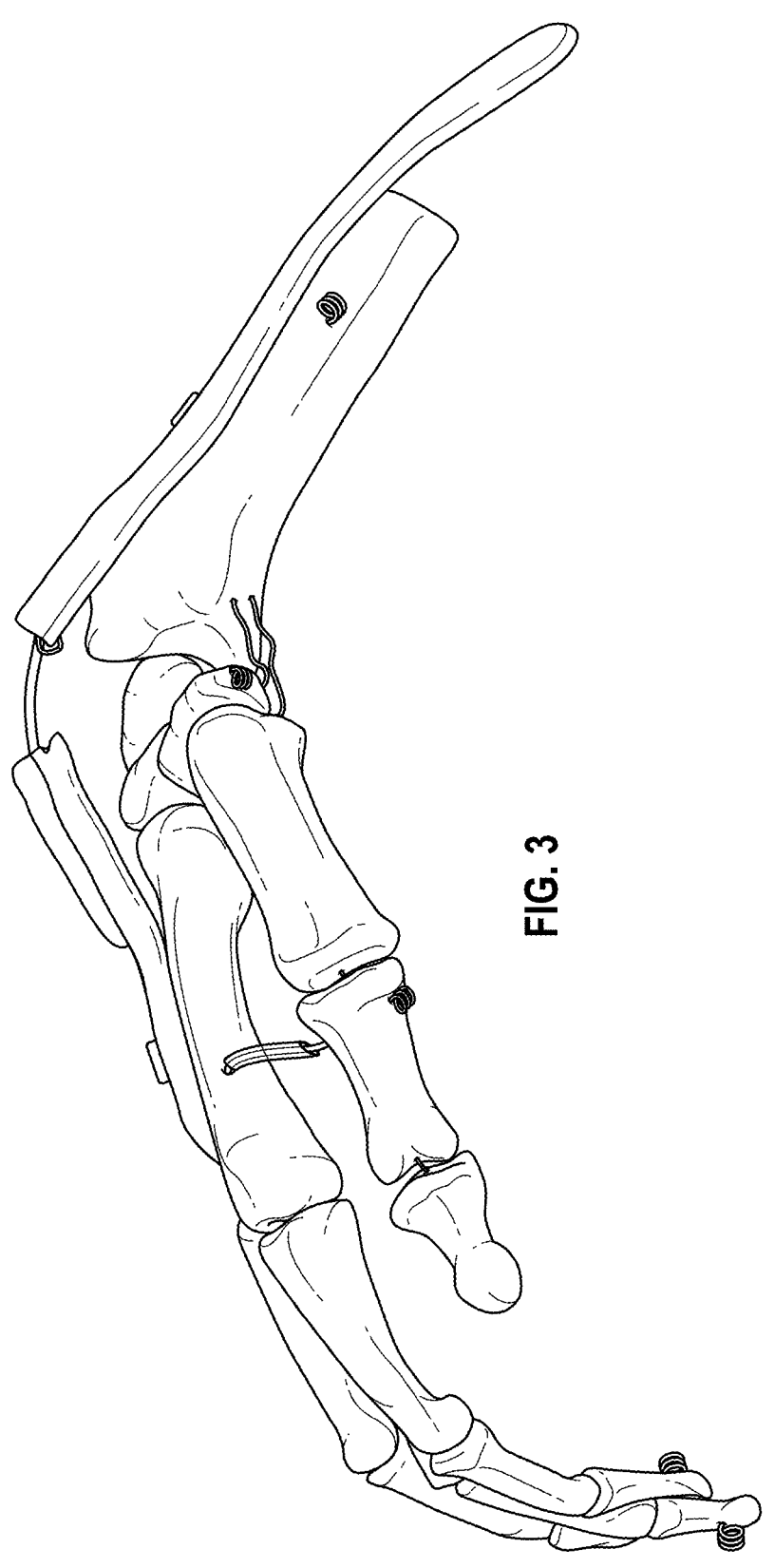
FIG. 3 is a photograph of a side view of a hinged dorsal spanning plate according to the present disclosure, fixed onto a model radio carpal joint, wherein the joint is held in a flexed position. In this view, the pistoning mechanism from one piece of the plate is in a lengthened or withdrawn configuration relative to the other piece.

In an aspect, the dorsal spanning plate assembly can also have a pistoning mechanism where one plate member, either proximal or distal, is configured to move in and out of the other plate member. Further in this aspect, the center of rotation of the pistoning mechanism can be at the center of radio-carpal joint; however, the plate member rests on a dorsal surface of the joint and is dorsal to the center of rotation. Thus, in an aspect, the plate member with the pistoning mechanism has more length when the wrist is in flexion and less length when the wrist is extended. In any of these aspects, the dorsal spanning plate assembly can incorporate a pistoning mechanism to accomplish this. In one aspect, the pistoning mechanism is viewable in its shorter and longer lengths in FIGS. 2 and 3, respectively.

Figure 4:
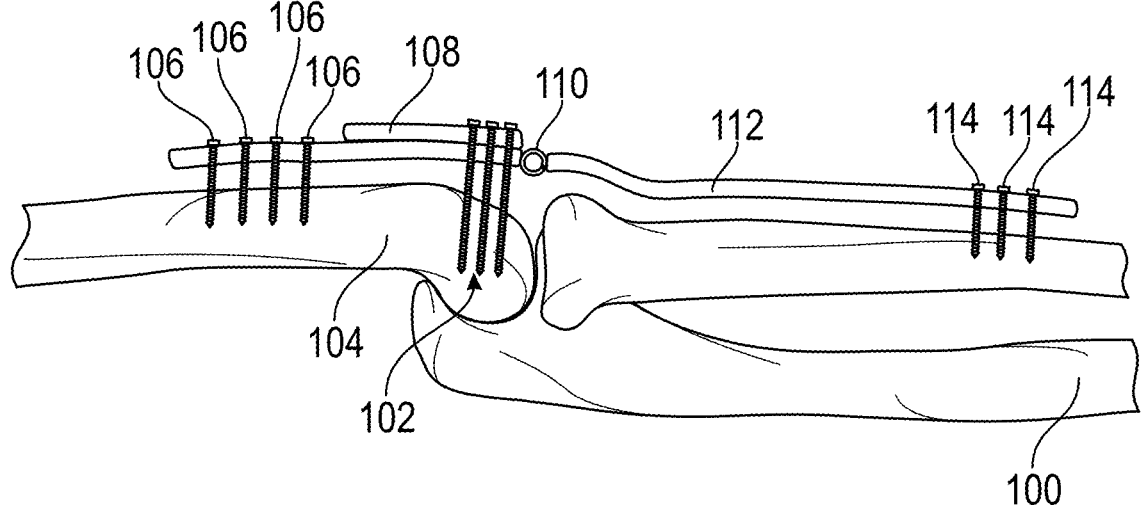
FIG. 4 is a drawing of a side view of a hinged dorsal spanning plate according to the present disclosure, fixed onto a model radio carpal joint, wherein the joint is held in a neutral position.

An exemplary embodiment is depicted in FIG. 4. Metacarpal bone 100 is attached to first plate member 112 by one or more screws 114. Hinge 110 connects first plate member 112 to second plate member 108. Optionally, additional screws, wires, or other connectors 102 may be used to stabilize the radius 104. Additional screws 106 secure second late member 108 to radius 104. A hinge joint is pictured as joint 110 but in some aspects, a ball-and-socket joint may be used.

In some aspects, the disclosed device is designed such that it does not cause damage or have adverse effects to the articular surfaces of the joint. In another aspect, the disclosed implant design ensures that ligaments and tendons that may come into contact with the implant are not compromised by excess material, rough surfaces, or sharp edges.

Method for Setting a Distal Radius Fracture

In an aspect, disclosed herein is a method for setting a distal radius fracture, the method including at least the steps of:

placing the dorsal spanning plate assembly described herein in close proximity to the distal radius fracture such that the first bone contacting surface is adjacent to at least one first bone of the subject and the second bone contacting surface is adjacent to a second bone in the subject;

attaching the first bone contacting surface to the at least one first bone using at least a first anchoring fastener; and attaching the second bone contacting surface to the second bone using at least a second anchoring fastener.

In one aspect, the first bone can be a metacarpal bone such as, for example, metacarpal III. In another aspect, the second bone can be a radius bone. In any of these aspects, the first anchoring fastener, the second anchoring fastener, or both, can be a bone screw.

In still another aspect, the dorsal spanning plate assembly can be removed after a period of from about 8 weeks to about 12 weeks, or after about 8, 9, 10, 11, or 12 weeks. In any of these aspects, the medical practitioner can perform X-rays or other examinations in order to assess the extent of bone healing prior to removing the plate.

In one aspect, the disclosed dorsal spanning plate assembly can be applied before, after, or during fixation of the fracture.

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

Definitions

A "fracture" as used herein is a complete or partial break in a bone. In order to heal a fracture, various strategies are employed. A fracture is said to be "reduced" or to undergo "reduction" when bone and/or bone fragments are brought back into alignment. A fracture is said to be "fixed" or to undergo "fixation" when bones and/or bone fragments are secured to one another.

"Muscle atrophy" refers to a loss in muscle mass and/or strength ("wasting"). In one aspect, muscle atrophy can occur in a joint immobilized (fixed) due to installation of a bone plate, since muscles around the joint cannot be used during the time the joint is immobilized.

As used herein, a "plate" or "plate assembly" refers to an orthopedic implant used to assist in correction of bone defects including, but not limited to, fracture. In a further aspect, a plate or plate assembly can be a temporary device attached to one or more bones or bone fragments to stabilize the bones, bone fragments, or a joint containing the same, until healing of the fracture.

A "dorsal spanning plate" is a device that allows for secondary bone healing in patients when it is not possible to achieve a stable reduction through a standard plate due to various factors including, but not limited to, fracture morphology, degree of comminution, poor native bone biology, and combinations thereof. In one aspect, a dorsal spanning plate or dorsal spanning plate assembly is fixed on the dorsal (non-palm) side of the hand.

"Load sharing" refers to a device, such as a dorsal spanning plate assembly, that does not carry all stress (as in the case of a "load-bearing" device) but transfers some small amount of stress to the bone itself, which can, in some aspects, trigger the processes necessary for bone healing. In one aspect, the dorsal spanning plate assembly disclosed herein is load sharing.

A "fastener" as used herein can be used to fix the dorsal spanning plate assembly to the bone or to otherwise provide stabilization. In an aspect, a fastener can be or include a bone screw, pin, staple, orthopedic (cerclage) wire, or any combination thereof. Meanwhile, a "setting fastener" is a component or device that fixes the joint in place after a plate or plate assembly is installed in a subject having a fracture, preventing any articulation or flexion of the joint during recovery. In one aspect, the disclosed device does not include a setting fastener. In an aspect, absence of a setting fastener allows a subject a full range of motion after placement of the dorsal spanning plate, which can speed recovery and reduce muscle atrophy.

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used in the specification and the appended claims, the singular forms "a," "an" and "the" include plural referents unless the context clearly dictates otherwise. Thus, for example, reference to "a screw," "a hole," or "a metacarpal bone," include, but are not limited to, collections of two or more such screws, holes, or metacarpal bones, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the terms "optional" or "optionally" means that the subsequently described event or circumstance can or cannot occur, and that the description includes instances where said event or circumstance occurs and instances where it does not.

Unless otherwise specified, temperatures referred to herein are based on atmospheric pressure (i.e. one atmosphere).

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

Examples

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Exemplary embodiments of the present disclosure are presented in FIGS. 1-4.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

What is claimed is:

1. A dorsal spanning plate assembly comprising:
a first plate member, wherein the first plate member comprises an elongated body defining a first longitudinal axis and including a first proximal end, a first distal end, a first bone contacting surface, and an opposite surface;
a second plate member, wherein the second plate member comprises an elongated body defining a second longitudinal axis and including a second proximal end, a second distal end, a second bone contacting surface, and an opposite surface and
a movable joint connecting the first proximal end to the second distal end, wherein the movable joint is configured to allow subject-directed movement of a radio carpal joint following implantation in a subject; and
wherein the dorsal spanning plate assembly does not include a setting fastener.

2. The dorsal spanning plate assembly of claim 1, wherein the first plate member and the second plate member each comprise one or more holes.

3. The dorsal spanning plate assembly of claim 2, further comprising one or more first screws extending through one of the one or more holes in the first plate member, wherein the one or more first screws are suitable for securing into a bone or bone fragment.

4. The dorsal spanning plate assembly of claim 2, further comprising one or more second screws extending through one of the one or more holes in the second plate member, wherein the one or more second screws are suitable for securing into a bone or bone fragment.

5. The dorsal spanning plate assembly of claim 1, wherein the movable joint comprises a hinge joint or a ball-and-socket joint.

6. The dorsal spanning plate assembly of claim 5, wherein the movable joint is a hinge joint and allows flexion and extension of the radio carpal joint in a subject.

7. The dorsal spanning plate assembly of claim 5, wherein the movable joint is a ball-and-socket joint and allows three-dimensional motion of the radio carpal joint in a subject.

8. The dorsal spanning plate assembly of claim 1, wherein the subject has a distal radius fracture.

9. The dorsal spanning plate assembly of claim 1, further comprising one or more additional stabilizing wires, pins, or connectors.

10. The dorsal spanning plate assembly of claim 1, further comprising a pistoning mechanism, wherein in the pistoning mechanism, the first plate member is configured to move in and out of an opening in the second plate member, or the second plate member is configured to move in and out of the first plate member.

11. The dorsal spanning plate assembly of claim 10, wherein a center of rotation of the pistoning mechanism is at a center point of the radio carpal joint.

12. The dorsal spanning plate assembly of claim 11, wherein the first plate member or the second plate member configured to move in and out of an opening is dorsal to a center of rotation of the dorsal spanning plate assembly.

13. The dorsal spanning plate assembly of claim 10, wherein the first plate member or the second plate member configured to move in and out of an opening has a greater length when the radio carpal joint is in flexion and a shorter length when the radio carpal joint is extended.

14. A method for setting a distal radius fracture, the method comprising:
placing the dorsal spanning plate assembly of claim 1 in close proximity to the distal radius fracture such that the first bone contacting surface is adjacent to at least one first bone of the subject and the second bone contacting surface is adjacent to a second bone in the subject;
attaching the first bone contacting surface to the at least one first bone using at least a first anchoring fastener; and
attaching the second bone contacting surface to the second bone using at least a second anchoring fastener.

15. The method of claim 14, wherein the first bone comprises at least one metacarpal bone.

16. The method of claim 15, wherein the at least one metacarpal bone is metacarpal III.

17. The method of claim 14, wherein the second bone comprises a radius bone.

18. The method of claim 14, wherein the first anchoring fastener, the second anchoring fastener, or both, comprise a bone screw.

19. The method of claim 14, further comprising removing the dorsal spanning plate assembly after a period of from about 8 weeks to about 12 weeks.

* * * * *